United States Patent [19]

Meserol

[11] Patent Number: 5,304,350
[45] Date of Patent: Apr. 19, 1994

[54] SLIDE TYPE ANALYTIC DEVICE, METHOD, AND PREPARATION APPARATUS

[75] Inventor: Peter M. Meserol, Montville, N.J.

[73] Assignee: Kloehn Instrument Inc., Brea, Calif.

[21] Appl. No.: 821,708

[22] Filed: Jan. 16, 1992

[51] Int. Cl.[5] ............................................. B01L 9/00
[52] U.S. Cl. ................................... 422/104; 422/55; 422/58; 422/67; 422/102; 436/46; 356/244
[58] Field of Search .............. 422/57, 102, 99, 64, 422/62, 104, 55, 58, 67; 436/46, 164; 356/246, 440, 436, 432, 244

[56] References Cited

U.S. PATENT DOCUMENTS

| | | | |
|---|---|---|---|
| 4,088,488 | 5/1978 | Lilja et al. | 422/57 |
| 4,441,793 | 4/1984 | Elkins | 359/398 |
| 4,519,981 | 5/1985 | Guigan | 422/64 |
| 4,569,647 | 2/1986 | McCormick | 422/99 |
| 4,738,824 | 4/1988 | Takeuchi | 436/46 |
| 4,761,381 | 8/1988 | Blatt et al. | 356/246 |
| 4,834,943 | 5/1989 | Yoshiyama | 422/62 |
| 4,978,503 | 12/1990 | Shanks et al. | 356/440 |
| 5,000,923 | 3/1991 | Coville et al. | 422/104 |
| 5,084,397 | 1/1992 | Siddons et al. | 422/99 |

Primary Examiner—James C. Housel
Assistant Examiner—Lien Tran
Attorney, Agent, or Firm—R. Gale Rhodes, Jr.

[57] ABSTRACT

Apparatus and method for depositing reagent only on a specimen contained in a cavity utilizing reagent deposition apparatus under the control of imaging apparatus providing an image of the specimen within the cavity; and an analytic implement including a pair of opposed and spaced apart transparent plates mounted in a frame and providing the cavity therebetween for receiving the specimen.

4 Claims, 3 Drawing Sheets

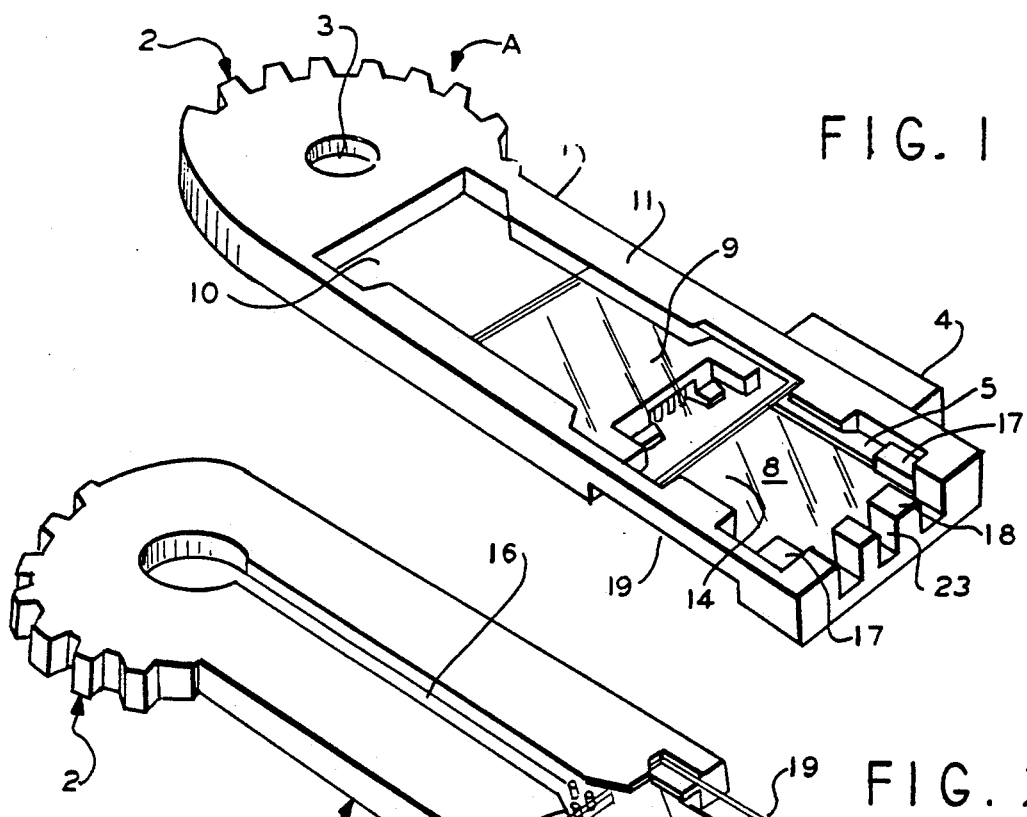
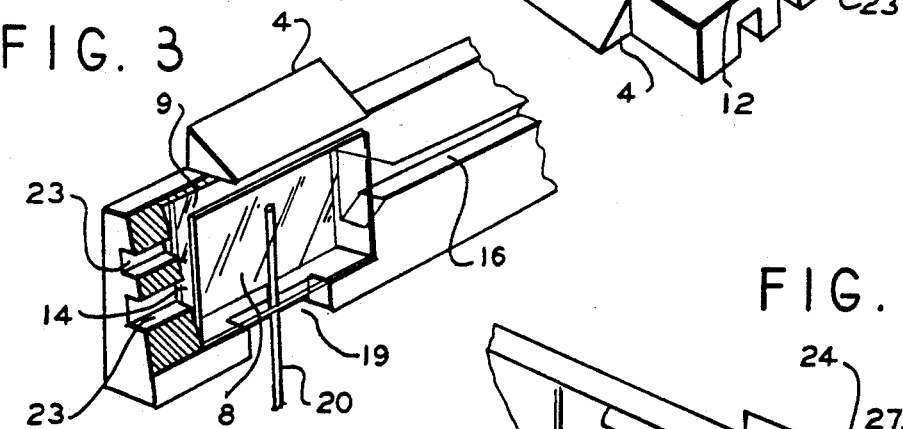
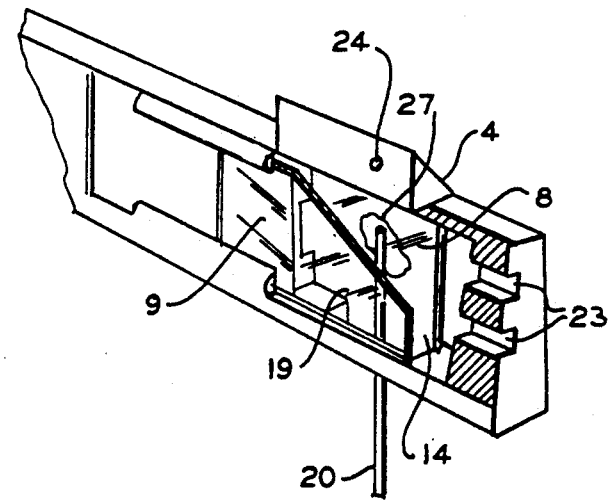

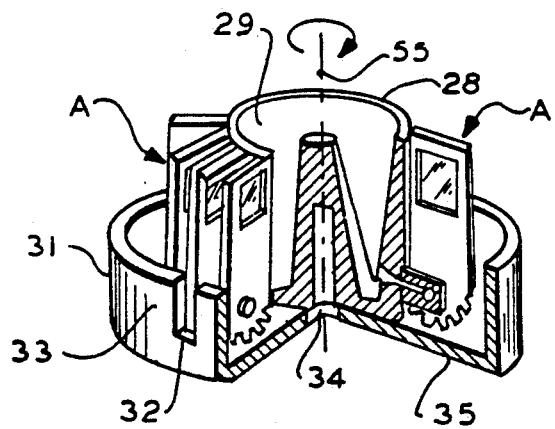
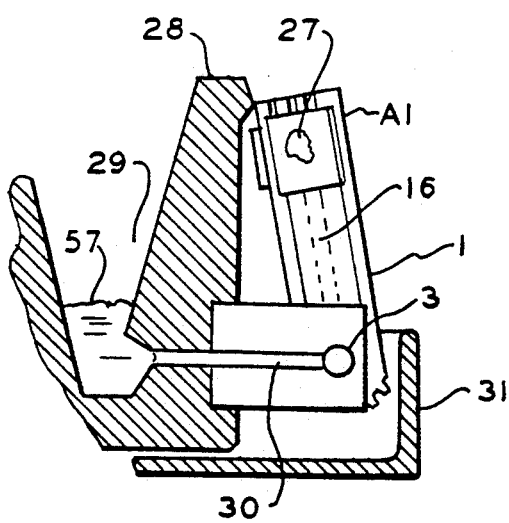
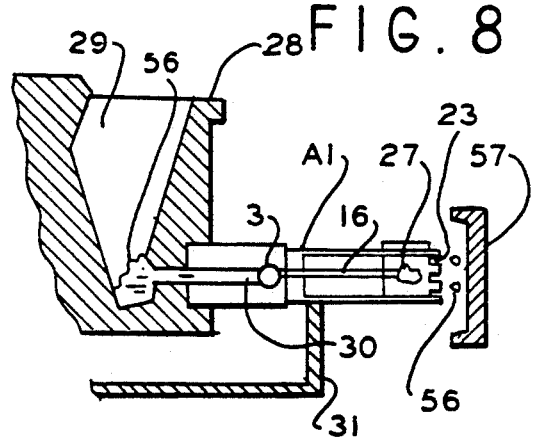
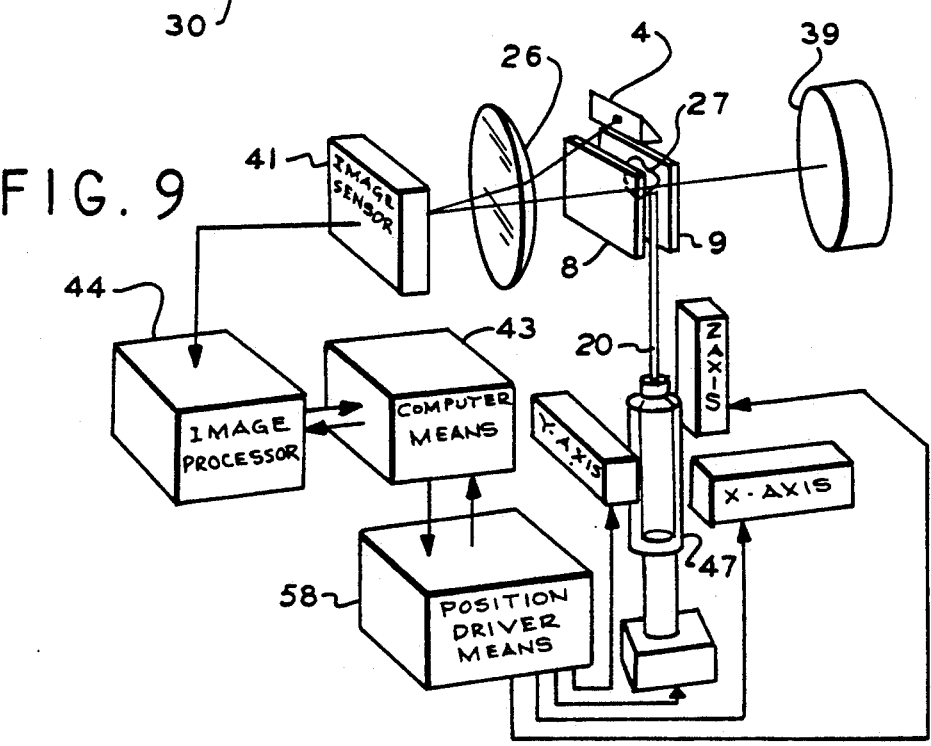

SLIDE TYPE ANALYTIC DEVICE, METHOD, AND PREPARATION APPARATUS

BACKGROUND OF THE INVENTION

1. Field of the Invention

This invention relates to the field of analytic devices, systems and methods, especially those performed on tissue specimens and body fluids deposited on glass slides, or contained between rigid planar glass or plastic sheets. More particularly, this invention addresses the introduction of reagent fluids to generate a reaction of interest with the specimen mounted or entrained within the cavity defined by parallel rigid optically transmissible plates.

Slide-based diagnostic procedures constitute the oldest class of in vitro analysis of specimens of clinical interest. The mounting of tissue or other sample on a planar glass surface for microscopic examination dates to the dawn of modern pathology. The enhancement of contrast in specimens has been accomplished by using staining chemicals which delineate the structure of the specimen. These cytology and histology stains have in the past been inexpensive chemicals which were applied to the specimen by total immersion of the slide. Wastage of stain fluid was not a consideration in these procedures.

Recent developments in biotechnology have yielded a class of staining reagents which are derived from recombinant DNA or monoclonal antibody production procedures. Unlike traditional cytology and histology reagents these are extremely costly and cannot be applied by immersion procedures. Conventional slide staining equipment cannot economically apply these reagents to slide-based specimens. The development of these extremely effective but costly reagents has defined a requirement for precision deposition of reagent materials on slide mounted or entrained specimens only in areas of procedural effectiveness. Currently this is accomplished manually. The economical and technical need for an automated means of accomplishing precision reagent deposition on specimens of this class is the stimulus for this invention.

2. Prior Art

Prior art citations describing parallel rigid plate specimen mounting or retention, and introduction of reactant materials include the following examples as an overview of the patent literature. Chediak (U.S. Pat. No. 2,561,339) describes a slide form comprising a separated parallel glass and plastic arrangement designed to receive specimens in discrete retention areas, and features a sliding cover plate. Wallace (U.S. Pat. No. 3,656,833) teaches a parallel plate laboratory slide apparatus employing a plurality of blind apertures molded into a plastic member mounted parallel to a glass substrate. The intent of this arrangement is to retain specimen and reactant. Meunier (U.S. Pat. No. 4,237,234) describes a radially arranged series of parallel plates between which specimen materials are placed. The device is representative of a class of laboratory test implements which employ centrifugal force to distribute or remove reactive agents from areas of interest. Cottingham (U.S. Pat. No. 4,596,695) discloses a slide-like reaction chamber which entrains particulate reagents between parallel plates, and introduces the reactants by means of capillary action. Lilja (U.S. Pat. No. 4,088,448) a planar cavity molded to define parallel walls in which a reactant fluid combination is introduced. Additionally, Meserol U.S. Pat. No. 4,400,353, issued to the inventor of this application, teaches a coplanar device in which the particulate reactant is caused to move and mix under rotation.

In the scientific literature, Badley, et al. reported a planar capillary device (Phil. Trans. Royal Soc. London. B 316, 143–160). Kronick and Little report a quartz plate planar cell assembly in Journal of Immunological Methods 8 (1975) 235–240. None of the cited prior art references employ a means of precision deposition under control of automata. There exists a need for a slide implement compatible with laboratory specimen forms such as sections or swab depositions, processed, prepared, and evaluated by an automated system capable of efficient reagent deposition in accordance with modern protocols and reagent formations.

SUMMARY OF THE INVENTION

A test article facilitating slide-based laboratory techniques, and an automated processing apparatus capable of precision fluid deposition on specimens mounted on the test article satisfying the foregoing need and embracing the present invention may include a single use slide arrangement comprising a molded polymer frame, a pair of parallel transparent rigid planar panels mounted therein, one of which is slidably mounted to expose the inner surface of an opposing fixed panel, at least one channel molded into the frame which permits fluid communication with a cavity formed between the opposing planar panels, at least one open side permitting ingress and egress of a computer controlled tubular probe into the cavity for the purpose of depositing reagents at selected sites within the cavity, such sites being selected by a video imaging system observing the position of the specimen, the position of the probe, and by means of computer analysis of the resultant images, cause the probe to deposit fluid reagents controllably pumped through the probe with precise and metered volumes and positions only on specimen materials mounted within the cavity, also determined by analysis of the changes in image generated by the deposition of the reagents.

DESCRIPTION OF THE DRAWINGS

FIG. 1 is a proximal view, in perspective, of an analytic implement embodying the present invention;

FIG. 2 is a distal view, in perspective, of the analytic implement of the present invention;

FIGS. 3 and 4 are perspective partial views of the analytic implement of the present invention;

FIG. 5 is a perspective view of a carousel comprising the present invention and shown loaded with a plurality of analytic implements of the present invention, and with a portion of the carousel being broken away and with portions shown in cross-section;

FIGS. 7 and 8 are partial cross-sectional views of a portion of the carousel of FIG. 5 showing a representative analytic implement in different positions; and FIG. 9 is an overall perspective view of apparatus embodying the present invention.

DESCRIPTION OF THE PREFERRED EMBODIMENT

Figure 6:
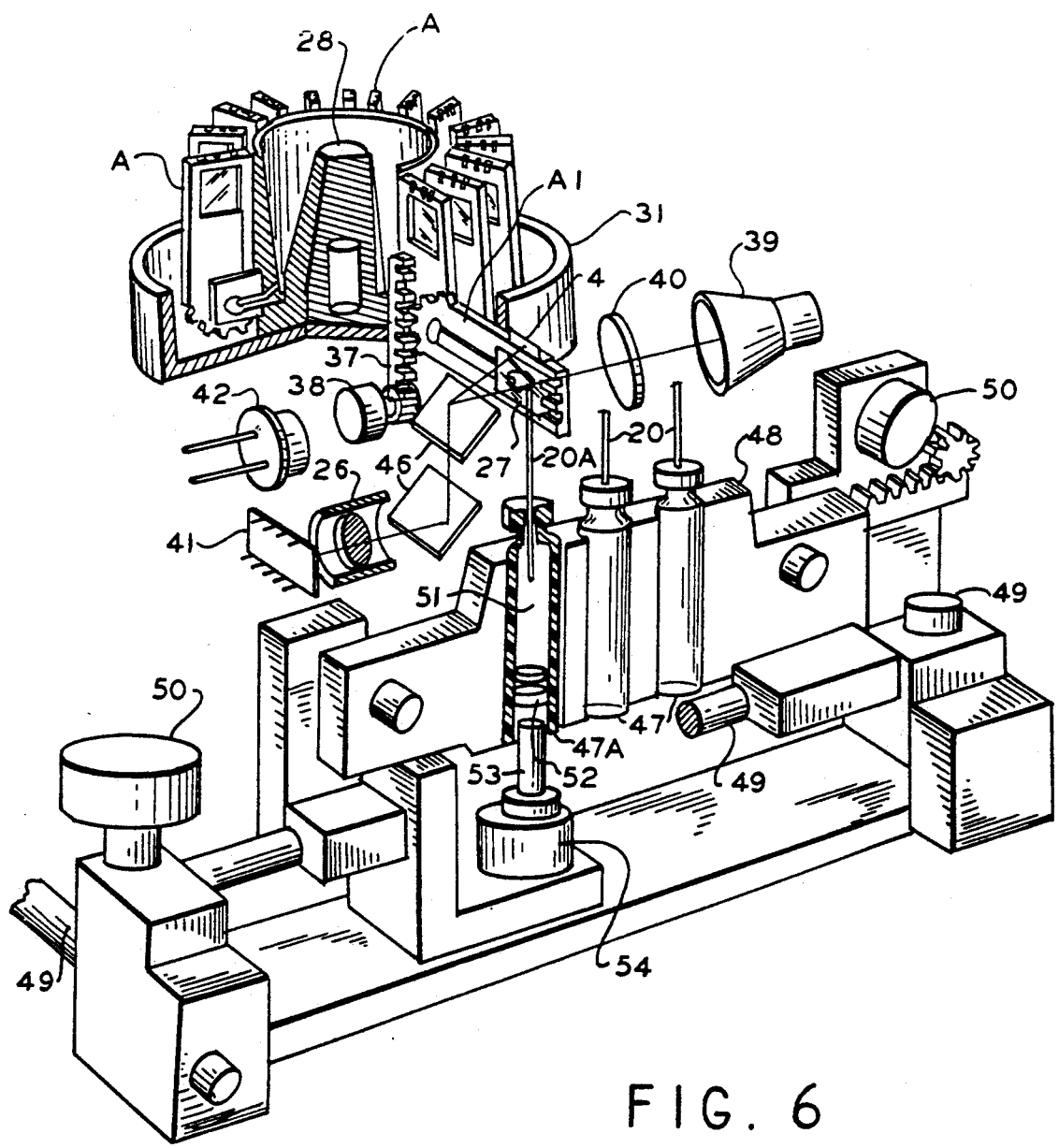
FIG. 6 is a perspective view of apparatus comprising the present invention.

With reference to the drawing figures an analytic implement, or test device, identified by general designation A and suitable for the practice of this invention is illustrated generally in FIGS. 1 and 2. FIG. 1 is a proximal view (side facing image sensor 41 in FIGS. 6 and 9) and FIG. 2 is a distal view (side facing light source 39 in FIGS. 6 and 9) of the analytic implement A which comprises a molded transparent polymeric frame (1) having formed in one end a gear sector (2) in the center of which is molded a pivot aperture (3), a prismatic form (4), and a rectangular aperture (5) at the opposite end. Planar rectangular glass or polymeric plates (8) and (9) are attached to the frame (1), in the case of the proximal plate (9), FIG. 1, by means of a rectangular channel (10) molded into the frame (1) and sized to slidably receive the plate (9) and which plate (9) is retained in the frame by grooved rails (11) permitting sliding movement of the plate (9) parallel to the frame (1) and with respect to the distal plate (8). The distal plate (8), FIG. 2, is fixedly received in a parallel position in the frame (1) covering the rectangular aperture (5) and is retained in the frame (1) by molded fingers (12). A fluid communicating channel (16), FIG. 2, is molded in to the frame (1) permitting fluid passage from the aperture (3) to a cavity (14) formed between the plates (8) and (9) when opposed and held in controlled separation by spacers (17), and when plate (9) is moved in position opposite plate (8) and against retainer stop (18); cavity 14 is for receiving a specimen. Flow diverting forms (13), e.g. a plurality of upwardly extending members, are molded in the channel (10) to widen a fluid stream to fill the cavity (14). A rectangular opening (19), FIGS. 3 and 4, formed in the frame (1) allows ingress and egress of a thin tubular probe (20), into and out of the cavity (14) formed between plates (8) and (9) as depicted in FIG. 3. Molded apertures (23) allow fluid egress from the cavity (14) under centrifugal forces when the implement is rotated at suitable speed about an axis opposite this aperture.

The position of the probe (20) within the cavity (14) is optically observable from the proximal face, i.e. through plate (9), through the prism form (4) which provides an image of the probe tip (24) to the imaging sensor means (41) by inclined mirrors (46) and through imaging lens (26); the image of the probe tip (24) is shown in FIG. 4. By this means the x, y and z position of the probe (20) within the cavity (14) can be determined from a single plane of observation. In operation the test implement A is initially arranged with the proximal plate (9) retracted away from the fixed plate (8) and no cavity is formed. A tissue or smear biological specimen (27), FIG. 4, is caused to be attached or deposited on the inner surface of the fixed plate (8) by means well known in histochemistry and microscopy. The proximal plate (9) is then moved or slid forward over the fixed plate (8) and against stop (18) thereby forming the cavity (14) between these plates and which cavity (14) has residing within it the specimen (27).

In FIG. 5 a plurality of implements A prepared with specimen as described above and shown in FIG. 4 is depicted and shown attached to a rotatable carousel (28) having a central reservoir (29) which has fluid communication channels (30), FIGS. 7 and 8, to the pivot aperture (3) in the implement frame (1). In FIG. 5 the analytic implements A are retained in a vertical position by means of cup (31) physically separate from and coaxial with the carousel (28); a circular opening (34) is provided in the cup bottom (35) through which the carousel (28) may be rotated and elevated. A single notch (32), FIG. 5, in the cup wall (33) allows individual implements A to pivot downward as the carousel (28) is rotated within the cup (31) to bring an individual implement A into registration with notch (32).

FIG. 6 depicts in particular a representative implement A1 and carousel (28) as operated upon by optical, mechanical, and fluid delivery apparatus necessary to practice the method of this invention. Carousel (28) and the test implements A are rotated by suitable means not shown but well known to the laboratory centrifuge art about a vertical axis (55), FIG. 5, through the carousel, and the test implement Al containing specimen (27) is indexed in registration with notch (32) (FIG. 5) in cup (31). A rack gear section (37) also in registration with the cup notch (32) engages the gear sector (2) of the test implement Al when the rack gear is driven upward by suitable motor means (38) to move the specimen (27) held between the transparent plates (8) and (9) into an optical focal plane defined by lens (26), transmissively illuminated by light source (39) and a filter or diffuser (40).

Image sensor (41), e.g. a suitable charge coupled device known to the art, FIGS. 6 and 9, receives the focussed image of specimen (27) and by suitable arrangement of beam splitting mirrors (46), FIG. 6, receives an image of the probe tip (24) through right angle prism (4). A plurality of tubular probes (20) are mounted on respective glass ampules (47). The ampules (47) are carried on a frame (48) which is movable in x, y and z axes along precision bearings (49) and driven by suitable positioning motors (50). By appropriate movement of the frame (48) along the x, y or z axes a probe (20) can be placed with great precision within the cavity (14) containing the specimen (27). When in the cavity (14) the probe tip (24) is imaged by above described components on image sensor (41), processed through suitable image processor 44 (suitable apparatus sometimes referred in the art as a frame grabber) and analyzed by image processing algorithm means within suitable computer means (43) allows the placement of the probe tip (24), through the position driver means 58 (comprised of suitable stepper device circuits known to the art) in intimate contact with the specimen (27) within the cavity (14). Reagent or staining materials (51) contained, for example, within the ampule (47a) are expelled through the probe (20a) and deposited only on the specimen (27) and retained there by capillary attraction forces between the specimen (27), and the inner and opposed sides or surfaces of plates (8) and (9). The explusion or expression of reagent materials (51), FIG. 6, is monitored and controlled by the computer means (43) acting in cooperation with the image sensor (41) and plunger motor means (54) driving plunger rod (53) and moving piston (52) within the ampule (47a) and thus expressing the reagent materials (51) of ampule (47a). By this method reagent is deposited only on the specimen (27) and not on areas within the cavity (14) not containing specimen.

The rack (37) is then operated by the motor (38) to return the implement Al to its vertical position shown in FIG. 5 after which the other implements A, FIG. 6, are sequentially indexed into registration with the notch (32) and reagent materials are sequentially deposited on the specimen contained in the other implements A. After the completion of reagent deposition on all specimen (27) contained in all of the implements A, all of the implements will all be returned to their vertical position as shown by representative implement A1 in FIG. 7 whereafter the carousel (28) is elevated by suitable means not shown which engage the underside of the carousel (28) through the opening (34) formed in the bottom of the cup (31) and the carousel (28) is elevated with respect to the cup (30), as illustrated by a representative implement Al in FIG. 8, and the carousel is then rotated by suitable means, not shown, to cause all of the implements A to pivot downwardly into the horizontal position shown with in FIG. 8 regard to representative implement A1 under the influence of centrifugal force; particularly it will be noted that such elevation of the carousel (28) with respect to the cup (31) causes the implements A to clear the upwardly extending wall (33) of the cup (31) as shown in FIG. 8.

Procedures in histological preparation often require sequential addition of reagent to specimens, and the washing of the specimen with buffer or other similar fluid in between such applications. Further, such protocols may require reagent removal and drying before subsequent reagent addition. The method and apparatus of the present invention permits this sequential procedure by centrifugal addition and removal of wash reagents as a complement to the controlled probe deposition of reagents which have a residence time in contact with the specimen, often at elevated temperatures.

FIG. 7 depicts a planar vertically displaced section through the carousel (28) and cup (31), with the analyte implement not shown in section, and FIG. 8 depicts the carousel (28) displaced upward with respect to the cup (31) and depicts the test implement Al moved outward under centrifugal force as the carousel is rotated about axis (55), FIG. 5. In FIG. 7 wash fluid 57 is shown in reservoir (29), and the cup (31) and carousel are at the lower position either at rest or in slow indexing position, with the cup (31) retaining the test implements in the vertical position. During centrifugation, FIG. 8, the wash fluid (56) is driven outward through fluid channels (30) into fluid channel (16) formed within the test implement frame (1), into and through the cavity (14) (FIGS. 3 and 4) containing specimen (27), and exiting through the molded apertures (23) and into a suitable collection means (57). This effectively washes the specimen with large volumes of wash fluid, and as centrifugation continues, extracts residual fluid from the specimen. Upon cessation of the centrifuge action, the carousel (28) is retracted downwardly into the cup (31) thus causing the outwardly extending analytic test implements A to engage the top portion of the cup wall (33) and be provided upwardly into the vertical position shown in FIG. 7, and permitting subsequent controlled probe reagent depositions as previously described. A sequenced series of these steps under program control permits preparation of stained slide specimens.

It is possible to measure optically active reagent depositions on the inner plate surfaces of the slide implement by means of both imaging and non-imaging sensoria. In FIG. 6, non-imaging optical sensor (42) could detect optical characteristics such as fluorescence, transmission, or luminescences stimulated by the light source (39) and appropriate excitation filters (40).

It will be understood by those skilled in the art that many modifications and variations may be made in the present invention without departing from the spirit and the scope thereof.

What is claimed is:

1. Apparatus for depositing reagent on a specimen, comprising:
   specimen holding means including opposed generally transparent members providing a cavity therebetween for receiving said specimen, said specimen occupying less than the entirety of said cavity;
   imaging means for providing an image of said specimen in said cavity;
   reagent deposition means for depositing reagent on said specimen in said cavity; and
   control means in response to said imaging means for controlling said reagent deposition means to produce relative motion between said specimen holding means and said reagent deposition means and to cause said reagent deposition means to deposit said reagent directly on said specimen residing in said cavity.

2. An analytic implement comprising:
   a frame;
   a pair of opposed, spaced apart, parallel transparent rigid planar plates mounted in said frame and providing a cavity therebetween for receiving a test specimen, said specimen occupying less than the entirety of said cavity;
   one of said plates mounted slidably in said frame for exposing the inner surface of the opposing panel upon relative movement therebetween;
   at least one channel molded into said frame for providing fluid communication with said cavity, said frame including opposed ends, one of said ends provided with rotational engagement means for positioning said analytic implement in a predetermined position and an aperture for permitting ingress of a fluid into said channel, and the other of said ends provided with at least one aperture permitting egress of said fluid from said channel;
   said frame including a side provided with an opening for permitting egress and ingress of a computer controlled tubular probe into and out of said cavity for the purpose of depositing reagent directly on said specimen residing in said cavity.

3. The analytic implement according to claim 2 wherein said rotational engagement means comprise a gear sector.

4. The apparatus according to claim 1 wherein said control means move said reagent deposition means relative to said specimen holding means.

* * * * *